(12) United States Patent
Baker et al.

(10) Patent No.: US 8,414,623 B2
(45) Date of Patent: Apr. 9, 2013

(54) CONNECTOR FOR CONNECTING ELONGATED MEMBERS

(75) Inventors: Douglas N Baker, Collierville, TN (US); Matthew Van Nortwick, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 140 days.

(21) Appl. No.: 12/915,955

(22) Filed: Oct. 29, 2010

(65) Prior Publication Data

US 2012/0109210 A1    May 3, 2012

(51) Int. Cl.
*A61B 17/70*    (2006.01)

(52) U.S. Cl.
USPC .......................................... 606/278; 606/264

(58) Field of Classification Search ........... 606/246–279
See application file for complete search history.

(56) References Cited

U.S. PATENT DOCUMENTS

| | | | | |
|---|---|---|---|---|
| 2008/0177315 A1* | 7/2008 | Usher | | 606/253 |
| 2008/0294195 A1* | 11/2008 | Egli et al. | | 606/246 |
| 2008/0306538 A1* | 12/2008 | Moore et al. | | 606/250 |
| 2008/0312692 A1* | 12/2008 | Brennan et al. | | 606/246 |
| 2008/0319484 A1* | 12/2008 | Fauth | | 606/247 |
| 2009/0005815 A1* | 1/2009 | Ely | | 606/246 |
| 2009/0024169 A1* | 1/2009 | Triplett et al. | | 606/248 |
| 2009/0030463 A1* | 1/2009 | Samudrala et al. | | 606/250 |
| 2009/0099604 A1* | 4/2009 | Cho et al. | | 606/250 |
| 2009/0216277 A1* | 8/2009 | Tornier et al. | | 606/250 |
| 2009/0228046 A1* | 9/2009 | Garamszegi | | 606/278 |
| 2009/0234391 A1* | 9/2009 | Butler et al. | | 606/278 |
| 2009/0254125 A1* | 10/2009 | Predick | | 606/264 |
| 2009/0264926 A1* | 10/2009 | Taylor et al. | | 606/246 |
| 2009/0264931 A1* | 10/2009 | Miller et al. | | 606/251 |
| 2009/0287253 A1* | 11/2009 | Felix et al. | | 606/278 |
| 2010/0094345 A1* | 4/2010 | Saidha et al. | | 606/250 |
| 2010/0274286 A1* | 10/2010 | Blain et al. | | 606/250 |
| 2010/0280552 A1* | 11/2010 | Lee | | 606/250 |
| 2011/0046675 A1* | 2/2011 | Barrus et al. | | 606/252 |
| 2011/0071569 A1* | 3/2011 | Black | | 606/250 |
| 2011/0087288 A1* | 4/2011 | Stevenson et al. | | 606/250 |
| 2011/0098748 A1* | 4/2011 | Jangra | | 606/278 |
| 2011/0106161 A1* | 5/2011 | Wilcox et al. | | 606/250 |
| 2011/0196425 A1* | 8/2011 | Rezach et al. | | 606/278 |
| 2012/0029567 A1* | 2/2012 | Zolotov et al. | | 606/264 |
| 2012/0029571 A1* | 2/2012 | Schwab et al. | | 606/278 |
| 2012/0035659 A1* | 2/2012 | Barrus et al. | | 606/251 |
| 2012/0109206 A1* | 5/2012 | Abdou | | 606/250 |
| 2012/0165874 A1* | 6/2012 | Biedermann et al. | | 606/278 |

* cited by examiner

*Primary Examiner* — Ellen C Hammond
*Assistant Examiner* — Stuart S Bray

(57) ABSTRACT

A connector for connecting together elongated members in a side-by-side arrangement. The connector includes a first receptacle for connecting to the first elongated member, and a second receptacle for connecting to the second elongated member. The angular position of the second receptacle may be adjustable relative to the first receptacle to accommodate the elongated members. Further, the connector may be configured to extend between the elongated members and the patient when the connector is implanted in a patient.

20 Claims, 4 Drawing Sheets

CONNECTOR FOR CONNECTING ELONGATED MEMBERS

BACKGROUND

The present application is directed to connectors for attaching together elongated members in a side-by-side arrangement and, more particularly, to connectors that have an adjustable receptacle.

The spine is divided into a variety of regions including the cervical, thoracic, and lumbar regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebrae that form the sacrum and the coccyx. The vertebrae of the spine are aligned in a curved configuration that includes a cervical curve, thoracic curve, and lumbosacral curve.

Various conditions may lead to damage of the intervertebral discs and the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Elongated members, such as rods, are often used in a variety of different surgical treatments to treat these conditions. In some cases, the elongated members are attached along the spine to facilitate spinal fusion to inhibit relative motion between vertebral members. In other cases, elongated members may be implanted with dynamic implants to preserve motion between vertebral members. Other treatments include implanting elongated members without the use of spinal fusion or dynamic implants.

Elongated members may provide a stable, rigid column that encourages bones to fuse after spinal-fusion surgery. Further, the members may redirect stresses over a wider area away from a damaged or defective region. Also, the members may restore the spine to its proper alignment. In the various surgical procedures, the members may be attached to the exterior of two or more vertebral members, whether it is at a posterior, anterior, or lateral side of the spine.

Two elongated members may extend along the same level of the spine. The members are in a side-by-side arrangement and laterally offset from one another. It may be advantageous to connect the members together to stabilize and provide additional support to the elongated members. However, previous connectors have not been effective in connecting together members in a side-by-side arrangement. The connectors have not been adjustable to accommodate the different members, particularly when the members extend along the spine at different angular orientations or have different elongated shapes (e.g., curved shaped, bent shape). Further, connecting the two members to a single connector may have previously caused unwanted stress to one or both members. This stress may be caused by the bending or manipulating of one or both members to force them into the connector.

SUMMARY

The present application is directed to connectors to connect first and second elongated members in a side-by-side arrangement within a patient. The connectors may include a body with a first side configured to face towards the patient when the connector is implanted in the patient. A first receptacle may extend through the body and may be positioned at a first end of the body. The first receptacle may be positioned above the first side with the first side positioned under the first receptacle when the connector is implanted in the patient. A second receptacle may be positioned at a second end of the body and above the first side with the first side positioned under the second receptacle when the connector is implanted in the patient. The second receptacle may include a perimeter wall that fully surrounds the second receptacle. The first receptacle may include an open side that is open on an opposite side of the first receptacle from the second receptacle. The first receptacle may be fixed relative to the body. The second receptacle may be rotatable relative to the first receptacle.

The connector may also include a body with a first side configured to face towards the patient when the connector is implanted in the patient and opposing lateral sides that extend upward away from the first side. The body may have a first receptacle configured to receive the first elongated member. The first receptacle may extend through the body with a centerline that extends through the opposing lateral sides. The first receptacle may be positioned upward from the first side and may include a back wall and an opposing open side that each extend between the opposing lateral sides. An annular section may be rotatably attached to the body and may be spaced away from the first receptacle. The annular section may include a wall that extends around and fully encloses a second receptacle. The annular section may be attached to the body with the second receptacle positioned upward beyond the first side of the body.

The application also includes methods of connecting together first and second elongated members in a side-by-side arrangement within a patient. The methods may include inserting the first elongated member into an open side of a first receptacle that is formed in a connector with the first elongated member extending outward beyond inferior and superior sides of the connector. The method may include positioning a first section of the connector underneath the first elongated member between the first elongated member and the patient. The method may include adjusting an angular position of a second receptacle relative to the first receptacle. The method may include inserting the second elongated member into the second receptacle with the second elongated member being contained within the second receptacle that extends fully around the second receptacle with the second elongated member extending outward beyond the superior and inferior sides of the connector. The method may include positioning a second section of the connector underneath the second elongated member between the second elongated member and the patient.

The various aspects of the various embodiments may be used alone or in any combination, as is desired.

DETAILED DESCRIPTION

Figure 1:
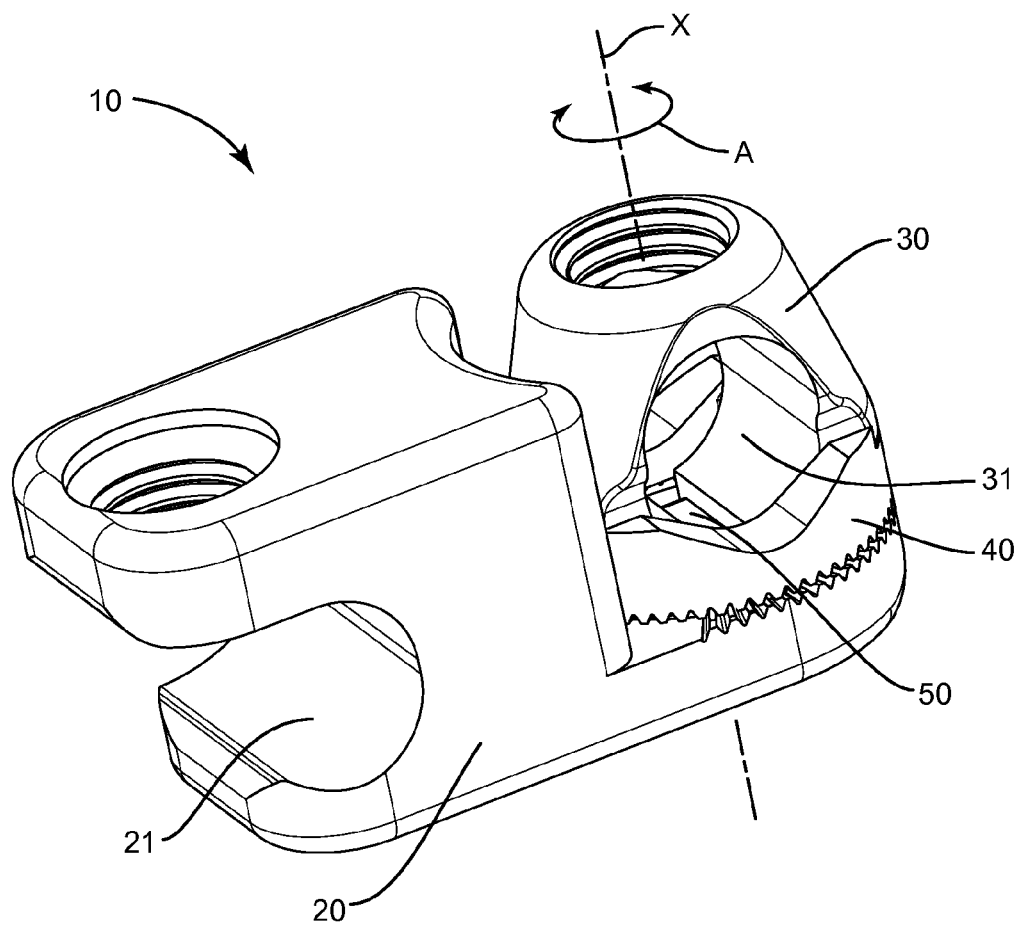
FIG. 1 is a perspective view of a connector.

The present application is directed to connectors for attaching together elongated members in a side-by-side arrangement. FIG. 1 illustrates a connector 10 with a first receptacle 21 to receive a first elongated member and an opposing second receptacle 31 to receive a second elongated member. The second receptacle 31 is configured to be adjustable about axis A as illustrated by arrow A.

Figure 2:
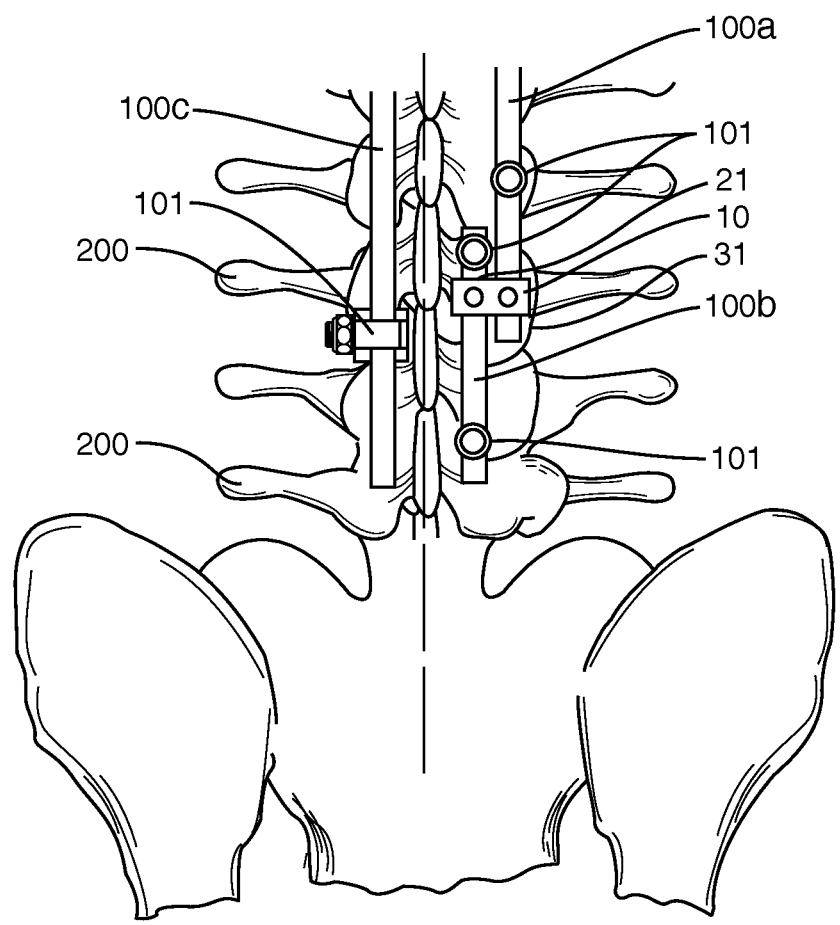
FIG. 2 is a posterior view of a connector positioned in a patient and connecting together two elongated members in a side-by-side arrangement.

FIG. 2 illustrates a connector 10 implanted in a patient and connecting together elongated members 100a, 100b. Each of the elongated members 100a, 100b extends along multiple levels of vertebral members 200 and are attached to the vertebral members 200 by anchors 101. The connector 10 extends between and connects the elongated members 100a, 100b in a side-by-side arrangement. In this embodiment, receptacle 21 connects with the elongated member 100b, and receptacle 31 connects with elongated member 100a. The second receptacle 31 is adjustable in the coronal plane and facilitates the connection between the members 100a, 100b.

Figure 3:
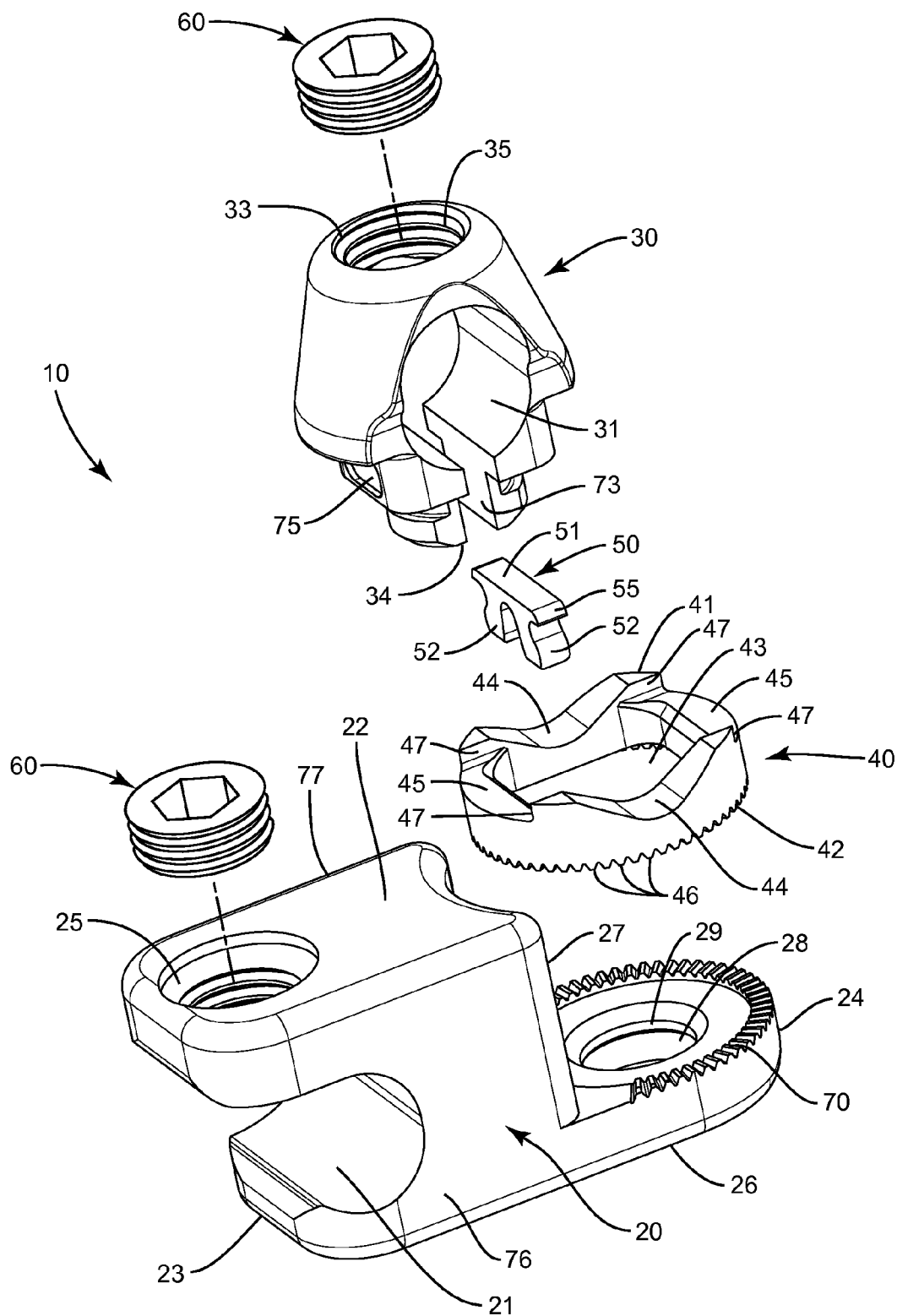
FIG. 3 is an exploded perspective view of a connector.
Figure 4:
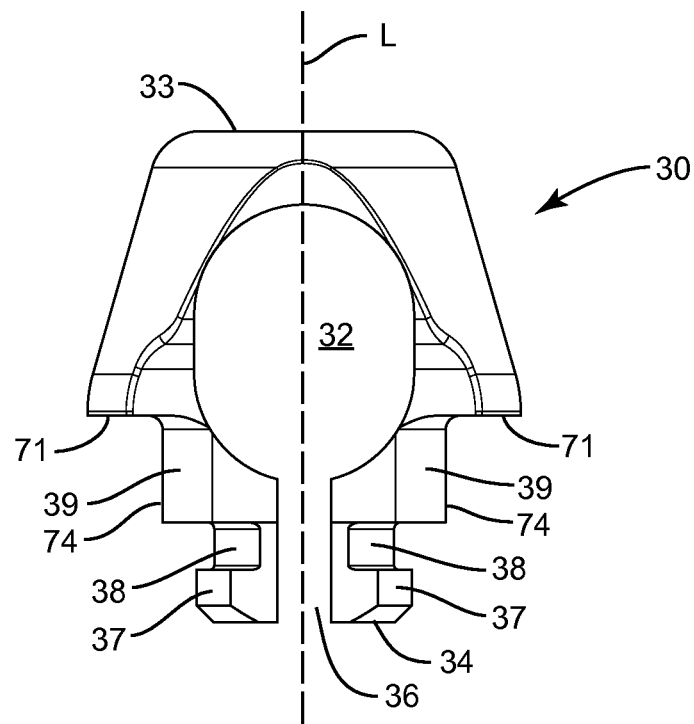
FIG. 4 is a side view of a body.
Figure 5:
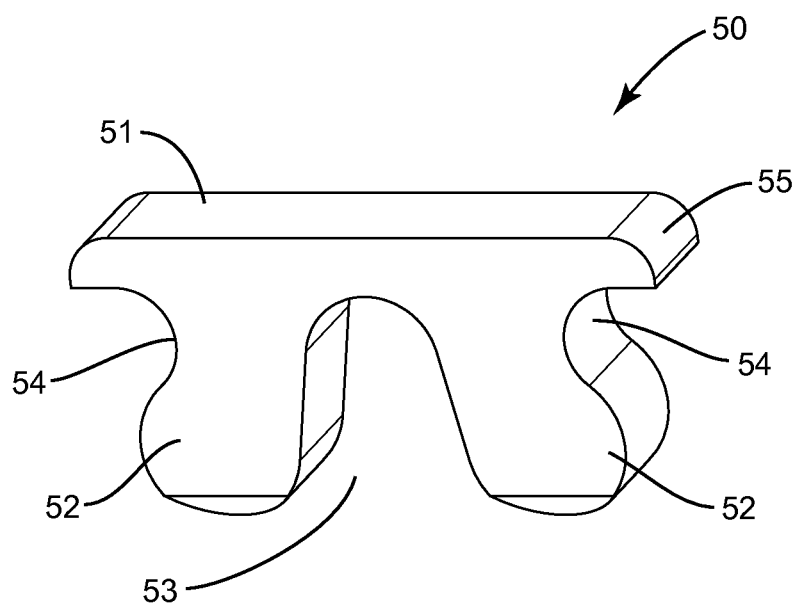
FIG. 5 is a perspective view of a clip.

FIG. 1 illustrates an assembled connector 10, and FIG. 3 illustrates an exploded view of a connector 10. The connector 10 generally includes a base 20, a body 30, an annular member 40, and a clip 50. The first receptacle 21 is formed by the base 20, and the second receptacle 31 is formed by the body 30 and annular member 40. As illustrated in FIG. 3, fasteners 60 may extend into each receptacle 21, 31 to maintain the respective elongated members 100 (for purposes of clarity, the fasteners 60 are not illustrated in FIG. 1).

The base 20 includes an elongated shape with a first end 23 and an opposing second end 24. The base 20 also includes a first side 26 and an opposing second side 22. The base 20 also include sides 76, 77 that extend between the sides 26, 22. When the connector 10 is positioned in the patient, the first side 26 may face towards the patient, one of the sides 76, 77 may face in a superior direction and the other side 76, 77 may face in an inferior direction. Further, the ends 23, 24 face in opposing lateral directions.

The first receptacle 21 is positioned at the first end 23 and extends through the sides 76, 77. The first receptacle 21 is further positioned between the opposing sides 22, 26. The receptacle 21 is positioned above side 26 such that a portion of the base 20 extends underneath the elongated member 100 in the patient. The first receptacle 21 further includes an open side at the first end 23 that faces outward away from the body 30 and annular member 40. The open side 23 allows the connector 10 to be attached at an intermediate portion of the elongated member 100 between the ends. An aperture 25 extends inward from the side 22 and into the first receptacle 21. The aperture 25 is threaded to receive one of the fasteners 60.

The base 20 also includes an aperture 28 that extends through the sides 22, 26 in proximity to the second end 24. The aperture 28 includes a tapered lip 29 that increases in height between the surfaces 22, 26 outward from the aperture 28. Splines 70 are positioned a greater radial distance outward from the aperture 28. Each of the splines 70 includes a straight shape and is aligned with the center of the aperture 28. The splines 70 may extend around a portion or entirety of the aperture 28. In one embodiment, the splines 70 extend around about half of the aperture 28.

The heights of the first and second ends 23, 24 measured between the sides 22, 26 are different. The first end 23 includes a greater height than the second end 24. A vertical wall 27 positioned between the ends 23, 24 extends between a first section of the side 22 at the first end 23 and a second section of side 22 at the second end 24. The wall 27 may be perpendicular to each of the sides 22, 26. The wall 27 may further include a curved shape with a concave face positioned towards the aperture 28.

The annular member 40 includes an aperture 43 that extends from a first side 41 to a second side 42. The first side 41 includes a pair of saddles 44 that are aligned on opposing sides of the aperture 43. Each saddle 44 includes a continuous curve with a maximum depth at a center of the aperture 43. The first side 41 also includes a pair of flat sections 45 that are aligned on opposing sides of the aperture 43. The flat sections 45 extend between walls 47 that form portions of the saddles 44. The aperture 43 may have a substantially rectangular shape with the saddles 44 being a lesser distance apart than the flat sections 45. The second side 42 of the annular member 40 includes splines 46 that are shaped and sized to engage with the corresponding splines 70 on the base 20.

The body 30 is rotatably connected to the base 20 and includes a longitudinal axis L that extends through first and second ends 33, 34. An aperture 32 is positioned within an interior of the body 30 between the ends 33, 34 and is substantially perpendicular to the longitudinal axis L. The aperture 32 forms a majority of the second receptacle 31.

The second end 34 is configured to engage with the base 20 and annular member 40. A gap 36 extends inward from the second end 34 and into the aperture 32. The surfaces 73 in the body 30 that define the gap 36 are substantially flat and aligned parallel to the longitudinal axis L. The gap 36 divides the second end 34 of the body 30 into first and second sections positioned on opposing sides of the longitudinal axis L. The gap 36 causes the sections to be deformable towards and away from the longitudinal axis L.

A first longitudinal section of the body 30 includes a pair of opposing ears 37. Ends of the ears 37 towards the second end 34 may be tapered to facilitate insertion into the aperture 28 of the base 20 as will be explained below. A second longitudinal section of the body 30 includes a neck 38 that is positioned inward from the ears 37. The neck 38 includes a narrower width measured perpendicular to the longitudinal axis L than the ears 37. The neck 38 includes an outer surface away from the longitudinal axis L that is substantially parallel to the axis L. A third longitudinal section of the body 30 includes first and second block sections 39. This third section includes a greater width than both the first and second sections. The block sections 39 include a side wall 74 spaced away from and substantially parallel to the longitudinal axis L. A shoulder 71 defines the extent of the block sections 39 and extends perpendicular to the longitudinal axis L and outward beyond the side wall 74. A cavity 75 may extend into one or both of the side walls 74.

The first end 33 of the body 30 includes an aperture 35 that extends into the aperture 32. The aperture 35 is sized to receive a fastener 60 that contacts against the elongated member 100. The aperture 35 may be threaded to engage with corresponding threads on the fastener 60.

The connector 10 is assembled with the aperture 43 of the annular member 40 being aligned with the aperture 28 of the base 20. The body 30 is then inserted into the apertures 43, 28. The width of the ears 37 of the body 30 is greater than the width of the opening 28. Therefore, during insertion, the force applied to the body 30 causes the ears 37 to deform inward towards the longitudinal axis L. The tapered ends of the ears 37 facilitate this inward movement. The ears 37 deform inward until the width is reduced to allow their passage through the aperture 28. Once the ears 37 move beyond the aperture 28, the ears 37 move back towards their original shape. This positions the ears below the lip 29 of the aperture 28 with the neck 38 aligned with the lip 29. The width of the ears 37 is again greater than the width of the aperture 28 thus preventing detachment of the body 30 form the base 20.

The insertion of the body 30 into the base 20 also positions the block sections 39 in the aperture 43 of the annular member 40. The rectangular shape of the block sections 39 and the aperture 43 cause the body 30 and annular member 40 to rotate together relative to the base 20.

A clip 50 is inserted into the gap 36 in the body 30. The clip 50 includes a flange section 55 with a pair of outwardly-extending prongs 52. The flange section 55 includes a relatively flat surface 51. The prongs 52 include a narrow neck section 54 that are positioned adjacent to the flange section 55. The prongs 52 are further separated by a gap 53.

The slip 50 is sized to fit in the gap 36 in the body 30. The surface 51 of the flange section 55 faces into the aperture 32. The prongs 52 are designed to flex inward to reduce in size to be inserted into the aperture 28 in a similar manner as the body 30. The insertion force causes the prongs 52 to move inward and reduce in width to fit through the aperture 28. Once inserted, the prongs 52 expand outward towards their original shape and are positioned below the neck 29 to connect the clip 50 to the base 20. Further, the neck 54 is aligned with the lip 29.

In a surgical procedure, the connector 10 is placed in a patient with the side 26 of the base 20 facing downward into the patient and the opposing side 22 facing outward. A first elongated member 100 is inserted into the open end of the first receptacle 21. A first fastener 60 is tightened into the aperture 25 and moves into contact with the first elongated member 100.

The second receptacle 31 is rotated relative to the first receptacle 21 to a position to receive the second elongated member 100. Once positioned, the second elongated member 100 is inserted through the second receptacle 31. The second receptacle 31 may be further rotated as necessary to accommodate the second elongated member 100. Once the second receptacle 31 is positioned as needed, a second fastener 60 is tightened into the aperture 35 and moved against the second elongated member 100. The tightening also forces the body 30 and annular member 40 downward towards the base 20. This downward movement causes the splines 46 on the annular member 40 to engage with and seat into the corresponding splines 70 on the base 20. Further, the body 30 and annular member 40 are locked in position relative to the base 20 to maintain the angular position of the second receptacle 31.

The adjustability of the second receptacle 31 accommodates the elongated members 100 at various orientations. This facilitates the process of connecting the connector 10. Further, this may prevent unwanted stresses from being applied to one or both elongated members 100.

The various steps of connecting the elongated member 100 may be performed in different orders. For example, the body 30 may be rotated and the elongated member 100 inserted into the second receptacle 31 prior to the elongated member 100 being inserted in the first receptacle 21. The fasteners 60 may not be tightened or even inserted in the corresponding apertures until both elongated members 100 are positioned in the receptacles 21, 31. The steps of the connection process may be done in various other orders.

The second receptacle 31 includes a wall that extends around and encloses the second receptacle 31. In one embodiment, the second receptacle 31 is formed by two or more separate elements, such as the body 30 and the annular member 40. These two elements together form the side wall that extends continuously around and encloses the second receptacle 31. In another embodiment, the second receptacle 31 is formed by a single element that contains and extends around the second receptacle 31.

FIG. 2 includes a connector 10 connecting together elongated members 100a, 100b that are both positioned on the same lateral side of the vertebral members 200. The connector 10 may also connect together elongated members at other locations relative to the vertebral members 200. In another embodiment, the connector 10 connects together elongated member 100b on a first lateral side of the vertebral members 200, and elongated member 100c on a second lateral side of the vertebral members 200. The connector 10 may extend through the interspinous space.

FIG. 1 illustrates the connector 10 used for during a vertebral surgical operation. The connector 10 may also be used in various other surgical settings in which elongated members 100 are connected together in a side-by-side arrangement. Examples include members 100 attached along a patient's long bones (e.g., femur, tibia, fibula, humerus).

Elongated members may include various different types of structures. These may include but are not limited to rods made from various materials including titanium, stainless steel, PEEK, cables, and wires.

The connector 10 may be used during surgical procedures on living patients. The connector 10 may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A connector to connect first and second elongated members in a side-by-side arrangement within a patient, the connector comprising:
    a body with a first side configured to face towards the patient when the connector is implanted in the patient, the body including an opening extending through the first side;
    a first receptacle that extends through the body and is positioned at a first end of the body, the first receptacle being positioned above the first side such that the first side is positioned under the first receptacle when the connector is implanted in the patient;
    a second receptacle positioned at a second end of the body and above the first side such that the first side is positioned under the second receptacle when the connector is implanted in the patient, the second receptacle including a flange configured for disposal in the opening to connect the second receptacle with the body, the second receptacle including a gap extending through the flange configured to allow the second receptacle to deform;

the first receptacle including an open side that is open on an opposite side of the first receptacle from the second receptacle, the first receptacle being fixed relative to the body;

the second receptacle being rotatable relative to the first receptacle.

2. The connector of claim 1, wherein the body includes first and second lateral sides that are spaced-apart and each extend upward above the first side, the first receptacle extends through each of the first and second lateral sides.

3. The connector of claim 2, wherein the first receptacle includes a back wall positioned opposite from the open side and opposing upper and lower walls that extend outward from the back wall towards the first end.

4. The connector of claim 3, wherein the open side of the first receptacle defines a first passageway, the first receptacle being positioned at the first end of the body, and an inner surface of the second receptacle defines a second passageway.

5. The connector of claim 1, wherein the connector includes a clip configured for disposal in the gap to prevent the second receptacle from deforming.

6. The connector of claim 5, wherein the second receptacle is connected to an annular member such that the second receptacle and the annular member are each rotatably connected to the body.

7. The connector of claim 1, further including a first aperture that extends into the first receptacle and a second aperture that extends into the second receptacle, each of the apertures being configured to receive a fastener.

8. A connector to connect first and second elongated members in a side-by-side arrangement within a patient, the connector comprising:

a body with a first side configured to face towards the patient when the connector is implanted in the patient and opposing lateral sides that extend upward away from the first side, the body including an opening extending through the first side;

the body having a first receptacle configured to receive the first elongated member and that extends through the body with a centerline that extends through the opposing lateral sides, the first receptacle positioned upward from the first side when the connector is implanted in the body and including a back wall and an opposing open side that each extend between the opposing lateral sides;

an annular member including a splined first surface engageable with a splined second side of the body opposite the first side such that the annular member is rotatably attached to the body and spaced away from the first receptacle; and a second receptacle including a bottom surface engageable with a second surface of the annular member opposite the first surface, the second receptacle including a flange configured for disposal in the opening to connect the second receptacle with the body, the second receptacle including a gap extending through the flange configured to allow the second receptacle to deform.

9. The connector of claim 8, wherein the body includes an elongated shape with first and second ends, with the open side of the first receptacle being positioned at the first end.

10. The connector of claim 9, wherein the first receptacle includes opposing upper and lower walls that extend outward from the back wall and towards the first end.

11. The connector of claim 8, wherein the annular member and the second receptacle are each rotatably connected to the body.

12. The connector of claim 8, wherein the annular member is a single element and the second receptacle is a single element that is separate from the annular member.

13. The connector of claim 8, further comprising a vertical wall positioned between the first and second receptacles.

14. The connector of claim 8, wherein the connector includes a clip configured for disposal in the gap to prevent the second receptacle from deforming.

15. A method of connecting together first and second elongated members in a side-by-side arrangement within a patient comprising:

inserting the first elongated member into an open side of a first receptacle that is formed in a connector body with the first elongated member extending outward beyond inferior and superior sides of the body, the body including an opening extending therethrough;

positioning a first section of the connector underneath the first elongated member between the first elongated member and the patient;

positioning a flange of the second receptacle within the opening to connect the body and the second receptacle;

adjusting an angular position of a second receptacle relative to the first receptacle;

inserting the second elongated member into the second receptacle with the second elongated member being contained within the second receptacle with the second elongated member extending outward beyond the superior and inferior sides of the connector; and positioning a second section of the connector underneath the second elongated member between the second elongated member and the patient.

16. The method of claim 15, further comprising tightening a fastener that extends into the second receptacle and locking the angular position of the second receptacle relative to the first receptacle.

17. The method of claim 15, further comprising contacting an inner surface of the second receptacle against the second elongated member.

18. The method of claim 15, further comprising positioning a first side of the connector that extends underneath both the first and second receptacles against the patient.

19. The method of claim 15, further comprising rotating the second receptacle relative to the first receptacle such that a centerline of the second receptacle is parallel with a centerline of the first receptacle.

20. The method of claim 15, further comprising rotating the second receptacle relative to the first receptacle such that a centerline of the second receptacle is non-parallel with a centerline of the first receptacle.

* * * * *